(12) United States Patent  
Sung et al.

(10) Patent No.: US 7,654,673 B2  
(45) Date of Patent: Feb. 2, 2010

(54) APPARATUS AND METHOD FOR DETERMINING EYESIGHT AGE

(75) Inventors: Gee-young Sung, Daegu-si (KR); Du-sik Park, Suwon-si (KR); Young-shin Kwak, Suwon-si (KR); Chang-yeong Kim, Yongin-si (KR); Kaida Xiao, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 11/830,234

(22) Filed: Jul. 30, 2007

(65) Prior Publication Data

US 2008/0030686 A1    Feb. 7, 2008

(30) Foreign Application Priority Data

Aug. 3, 2006  (KR) .................. 10-2006-0073383  
Nov. 7, 2006  (KR) .................. 10-2006-0109509

(51) Int. Cl.  
*A61B 3/02* (2006.01)  
*A61B 3/00* (2006.01)

(52) U.S. Cl. ....................... 351/223; 351/246

(58) Field of Classification Search .......... 351/205–246  
See application file for complete search history.

(56) References Cited

U.S. PATENT DOCUMENTS

| 6,125,213 | A * | 9/2000 | Morimoto | 382/263 |
| 6,570,997 | B2 * | 5/2003 | Noguchi | 382/100 |
| 2003/0177036 | A1 * | 9/2003 | Oka et al. | 705/2 |

FOREIGN PATENT DOCUMENTS

| JP | 2004-102359 | 4/2004 |
| JP | 2004-318632 | 11/2004 |
| JP | 2005-148880 | 6/2005 |

* cited by examiner

*Primary Examiner*—Mohammed Hasan  
(74) *Attorney, Agent, or Firm*—Staas & Halsey LLP

(57) ABSTRACT

An apparatus and method for determining an eyesight age, the apparatus including: a storage module to store at least one test image and age-specific response information for the at least one test image; a control module to receive user adjustment information indicating a variation in the at least one test image and to determine an eyesight age of a user based on the user adjustment information and the age-specific response information; and an output module to output the determined eyesight age.

47 Claims, 14 Drawing Sheets

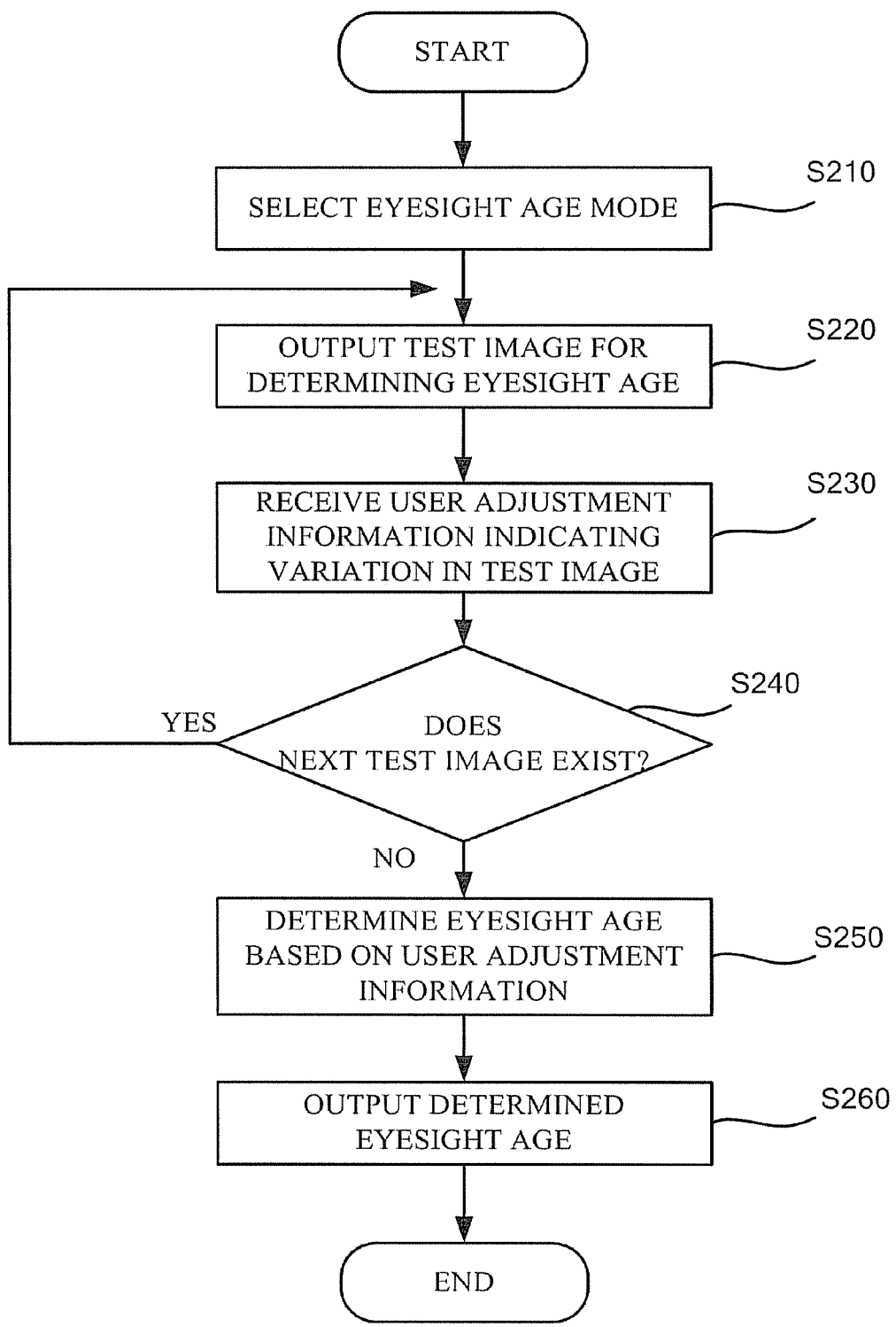

FIG. 4A
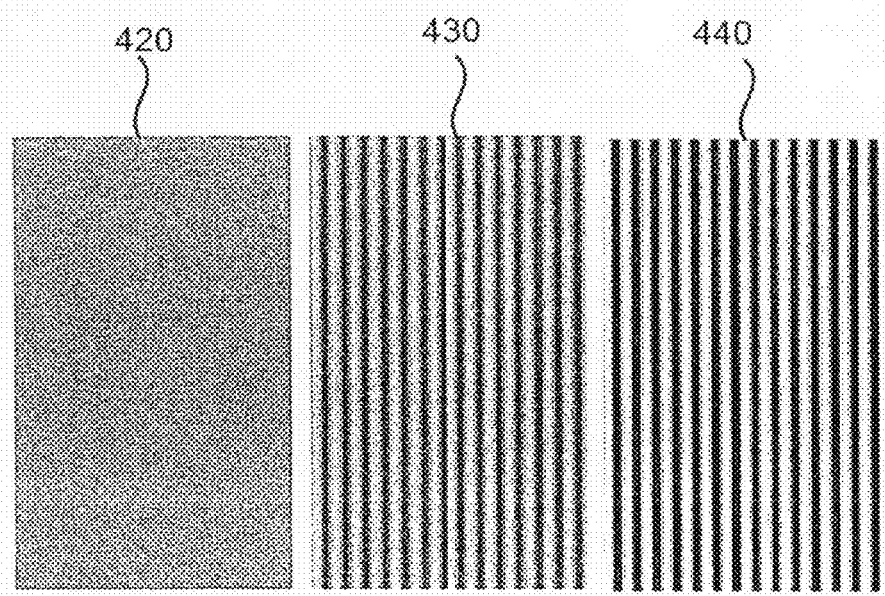
FIG. 4B
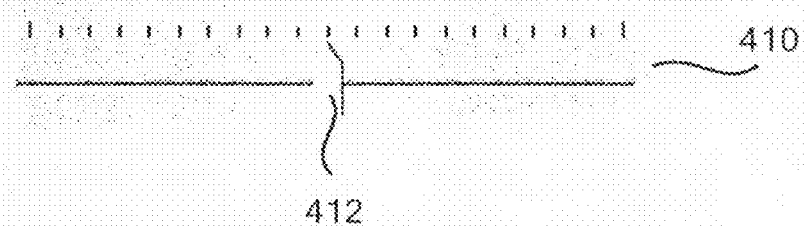
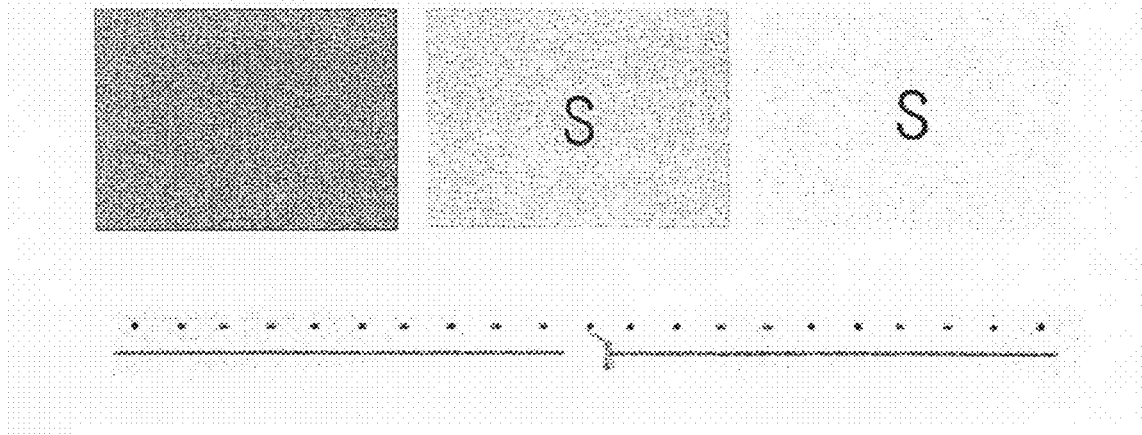

FIG. 5
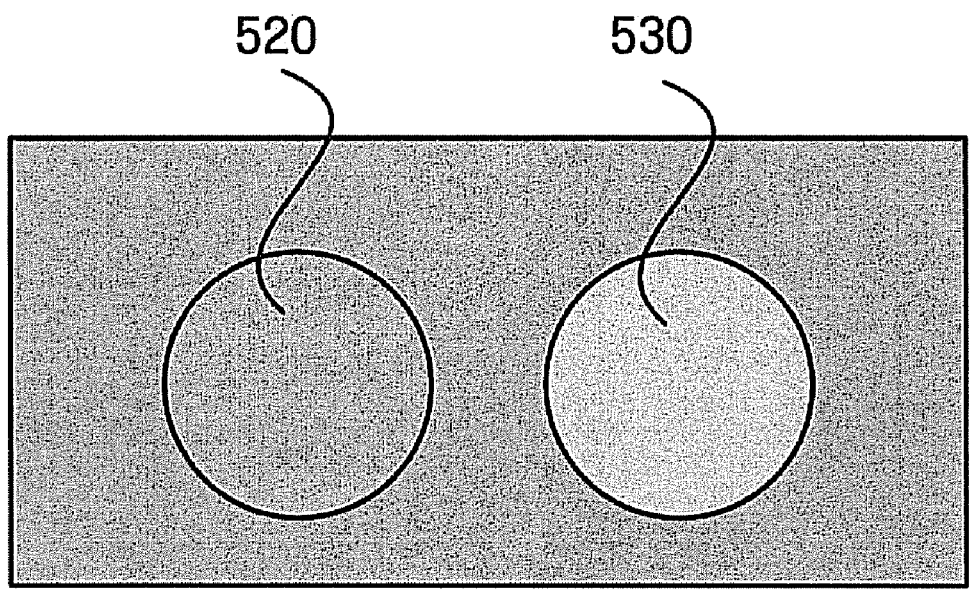
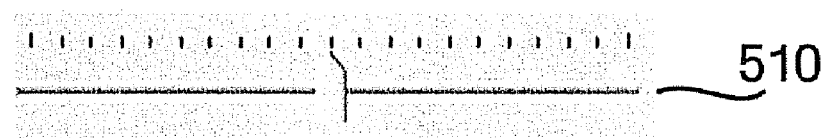

FIG. 6A
FIG. 6B
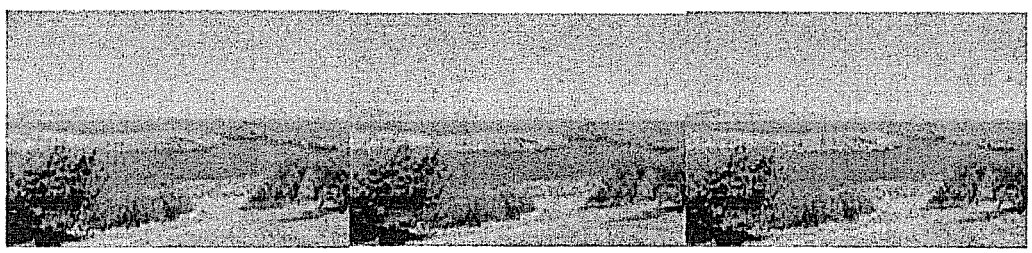

FIG. 9
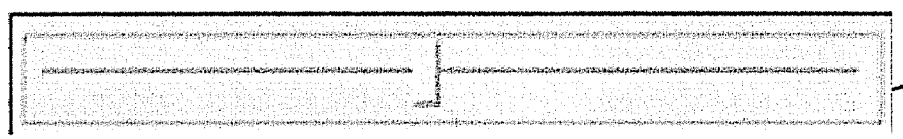

APPARATUS AND METHOD FOR DETERMINING EYESIGHT AGE

CROSS-REFERENCE TO RELATED APPLICATIONS

This application claims the benefit of Korean Application Nos. 2006-73383 and -2006-109509 filed on Aug. 3, 2006 and Nov. 7, 2006, respectively, in the Korean Intellectual Property Office, the disclosures of which are incorporated herein by reference.

BACKGROUND OF THE INVENTION

1. Field of the Invention

Aspects of the present invention relate to an apparatus and method for determining an eyesight age, and more particularly, to an apparatus and method for determining an eyesight age in which the eyesight age of a user can be determined using an image displayed by a display device.

2. Description of the Related Art

With recent developments in communication and digital signal processing technologies, various types of display devices (such as PC monitors, digital TVs, mobile phones, and personal digital assistants (PDAs)) have been developed.

Display devices not only display images or test data, but also provide users with a variety of entertainment functions. In addition, display devices can convert images through interaction with the users to satisfy the users' demands, and can display the converted images.

Specifically, display devices can determine the eyesight of a user and compensate when displaying the images according to the determined eyesight. Alternatively, given that eyesight gradually weakens as people age, display devices can compensate for images using a predefined method according to the age of a user.

However, the same image properties (e.g., hue, chroma, and contrast) may be felt differently regardless of eyesight. In addition, the degree to which eyesight weakens as a result of aging may vary from one individual to another.

Conventionally, display devices compensate for eyesight when displaying images simply by considering the characteristics of a user without any image properties taken into consideration. Thus, display devices may fail to properly reflect the degree of perception of images by a user.

Therefore, it is desirable to develop methods capable of reflecting the degree of perception of images by a user based on the properties of images displayed by a display device.

SUMMARY OF THE INVENTION

Aspects of the present invention provide an apparatus and method for determining an eyesight age in which the eyesight age of a user that reflects the degree of recognition of an image by the user can be determined using an image displayed by a display device.

Aspects of the present invention also provide an apparatus and method for determining an eyesight age, in which an image can be improved by adjusting the hue, chroma, and/or contrast of the image.

According to an aspect of the present invention, there is provided an apparatus for determining an eyesight age, the apparatus including: a storage module to store at least one test image and age-specific response information for the at least one test image; a control module to receive user adjustment information indicating a variation in the at least one test image and to determine an eyesight age of a user based on the user adjustment information and the age-specific response information; and an output module to output the determined eyesight age.

According to another aspect of the present invention, there is provided an apparatus for determining an eyesight age, the apparatus including: a user input module to receive user input information; an image adjustment module to modify an image according to the user input information; an image display module to display the modified image; and an eyesight output module to output an eyesight age corresponding to the user input information if the user input information is uniformly maintained for a predetermined amount of time.

According to yet another aspect of the present invention, there is provided a method of determining an eyesight age, the method including: receiving user adjustment information indicating a variation in at least one test image; determining an eyesight age of a user based on the user adjustment information and age-specific response information; and outputting the determined eyesight age.

According to still another aspect of the present invention, there is provided a method of determining an eyesight age, the method including: receiving user adjustment information indicating a variation in at least one test image; determining an eyesight age of a user based on the user adjustment information and age-specific response information; determining an image enhancement parameter based on the determined eyesight age and image information of an original input image; modifying the original input image according to the image enhancement parameter; and outputting the modified image.

According to another aspect of the present invention, there is provided a method of determining an eyesight age, the method including: receiving user input information; modifying an image according to the user input information and displaying the modified image; and outputting an eyesight age corresponding to the user input information if the user input information is uniformly maintained for a predetermined amount of time.

According to yet another aspect of the present invention, there is provided an apparatus for determining an eyesight age, the apparatus including: a storage module to store at least one test image and age-specific response information for the at least one test image; a control module to receive user adjustment information indicating a variation in the at least one test image, and to determine an eyesight age of a user based on the user adjustment information and the age-specific response information; an image compensation module to determine an image enhancement parameter based on the determined eyesight age and image information of an original input image, and to modify the original input image according to the image enhancement parameter; and an output module to output the modified image provided by the image compensation module.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 2 is a flowchart illustrating a method of determining an eyesight age according to an embodiment of the present invention;

FIGS. 4A and 4B present test images having contrast patterns;

FIG. 5 presents a test image for adjusting chroma;

FIGS. 6A and 6B present test images for determining user preferences;

FIG. 9 is a diagram explaining a determining of an eyesight age according to another embodiment of the present invention;

DETAILED DESCRIPTION OF THE EMBODIMENTS

Figure 1:
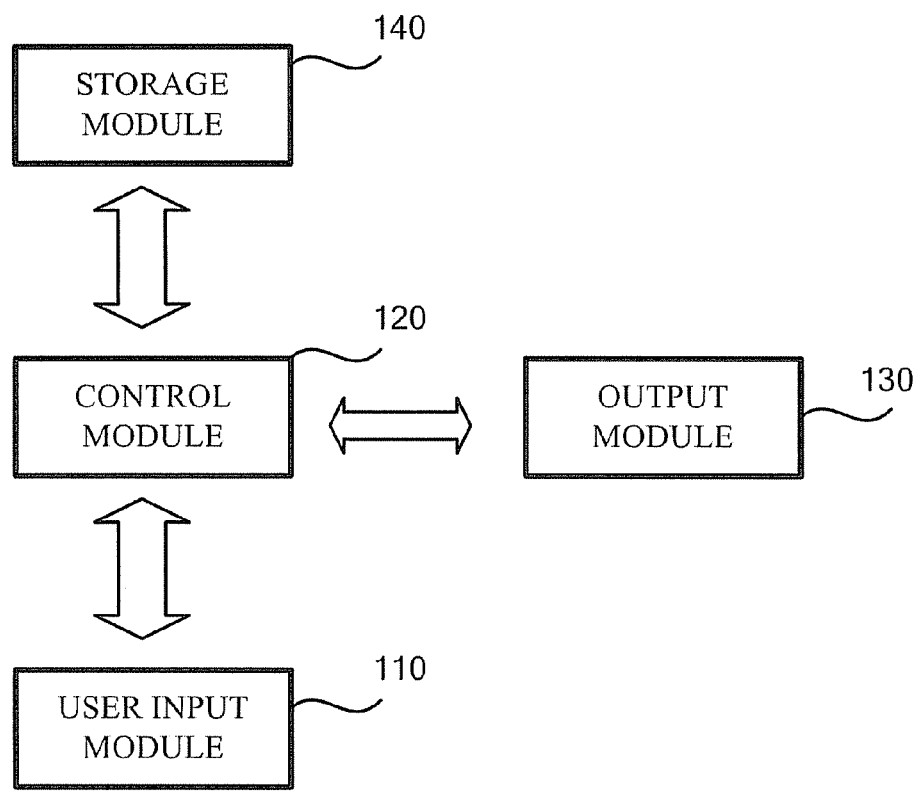
FIG. 1 is a block diagram of an apparatus for determining an eyesight age according to an embodiment of the present invention.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Aspects of the present invention are described hereinafter with reference to flowchart illustrations of user interfaces, methods, and computer program products according to embodiments of the invention. It will be understood that each block of the flowchart illustrations, and combinations of blocks in the flowchart illustrations, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create methods and/or devices for implementing the functions specified in the flowchart block or blocks.

These computer program instructions may also be stored in a computer-usable or computer-readable memory that can direct a computer or other programmable data processing apparatus to function in a particular manner, such that the instructions stored in the computer-usable or computer-readable memory produce an article of manufacture including instruction means that implement the function or functions specified in the flowchart block or blocks.

The computer program instructions may also be loaded onto a computer or other programmable data processing apparatus to cause a series of operations to be performed on the computer or other programmable apparatus to produce a computer-implemented process such that the instructions that execute on the computer or other programmable apparatus provide operations for implementing the functions specified in the flowchart block or blocks.

And each block of the flowchart illustrations may represent a module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

The term "eyesight age," as used herein, refers to an index indicating the degree of recognition of an image by a user. An eyesight age is clearly differentiated not only from the age of a user, but also from the eyesight of a user, which results from an abnormal refraction of the eye.

FIG. 1 is a block diagram of an apparatus 100 for determining an eyesight age according to an embodiment of the present invention. Referring to FIG. 1, the apparatus 100 includes a user input module 110, a control module 120, an output module 130, and a storage module 140. The user input module 110 receives user input information from a user. The storage module 140 stores test images for determining an eyesight age. The control module 120 calculates the eyesight age of the user based on user adjustment information that reflects a variation in a test. The output module 130 outputs a test image and the result of the calculation performed by the control module 120.

The user input module 110 may include a variety of input tools and/or devices and receive user input information from the user using the input tools and/or devices. Examples of the input tools and/or devices include a keypad, buttons, a touch screen, a mouse, a keyboard, a joystick, a metal-dome switch, and a wireless remote control. A user may switch the apparatus 100 to a mode for determining an eyesight age or select a test image from among a plurality of test images by using the user input module 110.

The storage module 140 stores at least one test image and age-specific response information for each of the at least one test image.

The control module 120 varies a test image stored in the storage module 140, and determines the eyesight age of the user based on user adjustment information input thereto via the user input module 110. The control module 120 may determine the eyesight age of the user by comparing the user adjustment information with response information stored in the storage module 140.

The term 'module', as used herein, refers to, but is not limited to, a software or hardware component, such as a Field Programmable Gate Array (FPGA) or Application Specific Integrated Circuit (ASIC), which performs certain tasks. A module may be configured to reside on the addressable storage medium and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

The operations of the user input module 110, the control module 120, the output module 130, and the storage module 140 will hereinafter be described in further detail with reference to FIG. 2. Referring to FIGS. 1 and 2, first, a user chooses an eyesight age mode for determining an eyesight age using the user input module 110 in operation S210. Then, the control module 120 extracts a test image for determining an eyesight age from the storage module 140 and controls the output module 130 to output the extracted test image in operation S220.

The user may continuously vary characteristics of a test image using an input tool and/or device of the user input module 110 (e.g., four direction keys or number buttons), and arbitrarily choose a test image obtained by the variation. For example, referring to FIG. 3A, the user may continuously vary the color of a Landolt C 320 in a test image 300 without changing the color of a background screen 310 of the test image 300. Then, the user may press a predetermined button on the user input module 110 when the user determines that the Landolt C 320 is properly recognized during the variation of the color of the Landolt C 320. In this manner, the user can choose a preferred test image.

In operation S230, user adjustment information regarding the user's modification of a test image (operation S220) is input to the control module 120 via the user input module 110. The user adjustment information may include both a test image selected by the user and color information of the selected test image.

In operation S240, the control module 120 determines whether there is another test image to be output for determining the eyesight age.

In operation S250, if no other test images exist (operation S240), the control module 120 determines the eyesight age of the user based on the user adjustment information. The determination of the eyesight of the user by the control module 120 will hereinafter be described in further detail with reference to FIGS. 3A through 3C.

Figure 3A:
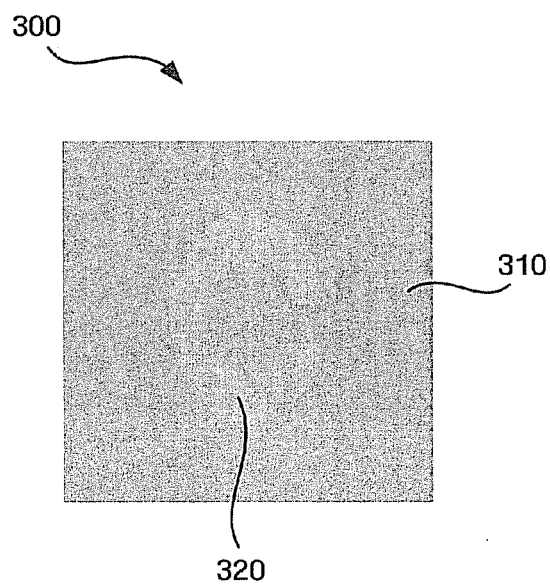
FIGS. 3A through 3C are diagrams explaining the method illustrated in FIG. 2, according to an embodiment of the present invention.
Figure 3B:
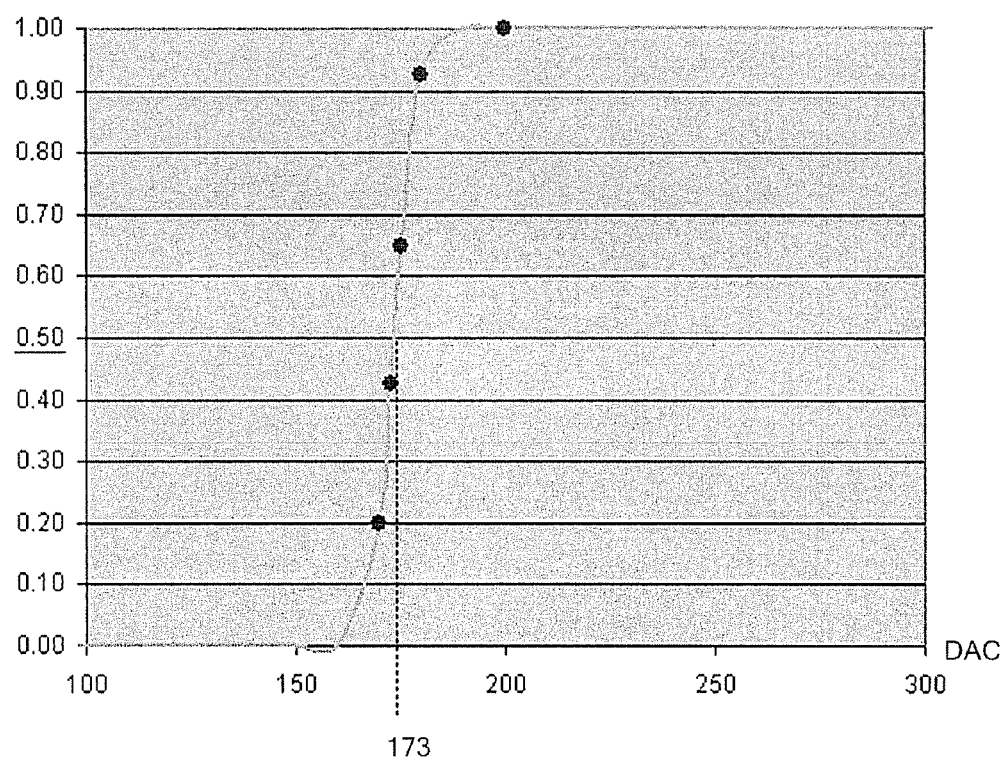

Referring to FIG. 3A, the test image 300 includes the background screen 310 and the Landolt C 320. Age-specific response information for the test image 300 is stored in the storage module 140 in advance. The generation of the response information will hereinafter be described in detail.

According to aspects of the present invention, the eyesight age of a user is determined based on the fact that as people age, their eyes become duller in terms of sensing the color of blue. Assuming that each of red, green, and blue (RGB) includes eight bits, color information of the background screen 310 and the Landolt C 320 is initially set as follows: (R, G, B)=(160, 160, 160). Thus, the background screen 310 and the Landolt C 320 cannot be differentiated from each other. Blue (B) information of the Landolt C 320 is varied from 161 to 255 while uniformly maintaining color information of the background screen 310 and red (R) and green (G) information of the Landolt C 320. As a result, the Landolt C 320 becomes bluish and appears as such in a gray background. Blue information that is transformed will hereinafter be referred to as DAC. A user can correctly determine the shape and an open direction of the Landolt C 320 at some point during the variation of DAC of the Landolt C 320. The open direction of the Landolt C 320 may be varied according to DAC.

The probability of a user properly recognizing the open direction of the Landolt C 320 at a certain DAC level is referred to as a correct answer probability. According to the present embodiment, an experiment is performed on a number of people of the same age, thereby obtaining a graph illustrated in FIG. 3B indicating the relationship between a correct answer probability and DAC.

A DAC value corresponding to a correct answer probability of 50% varies according to the age of people who are subject to the aforementioned experiment. In general, the DAC value corresponding to a correct answer probability of 50% increases according to the age of people, as indicated by a graph of FIG. 3C. The graph illustrated in FIG. 3C can be obtained based on the graph illustrated in FIG. 3B indicating the relationship between a correct answer probability and DAC for each age.

Figure 3C:
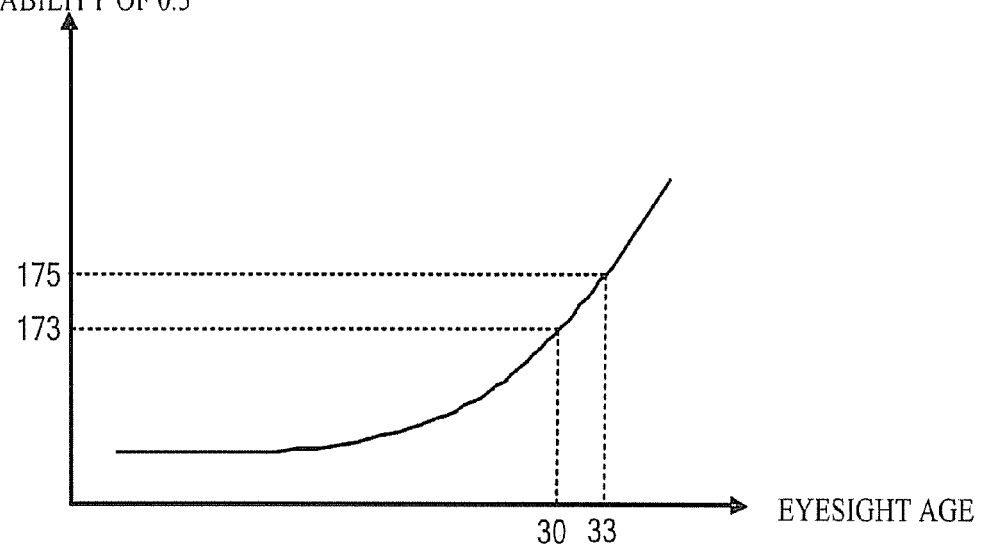

The graph illustrated in FIG. 3C may correspond to age-specific response information regarding the test image 300. For example, referring to FIG. 3B, the DAC value corresponding to a correct answer probability of 50% is approximately 173. Referring to FIG. 3C, the DAC value of 173 corresponds to an eyesight age of 30. DAC (on the y-axis) may be represented as luminance. That is, a DAC difference between the background screen 300 and the Landolt C 320 can be represented as a difference between the luminance of the background screen 300 and the luminance of the Landolt C 320. Therefore, the experimental results illustrated in FIGS. 3B and 3C can be applied to display devices having luminance properties different from the display device used to produce the corresponding experimental results. For example, if DAC=173, an eyesight age may be determined to be 30. However, this determination can only be applied to display devices having the same properties as the display device used to produce the experimental results illustrated in FIGS. 3B and 3C. However, by representing DAC as luminance, the experimental results illustrated in FIGS. 3B and 3C can be applied to display devices having luminance properties different from the display device used to produce the corresponding experimental results.

Once age-specific response information regarding the test image 300 is obtained in the aforementioned manner, the age-specific response information is stored in the storage module 140. Then, when the test image 300 is displayed by the output module 130 (operation S220 in FIG. 2), user adjustment information is input by a user (operation S230). For example, if a user whose age is 30 is able to correctly determine the open direction of the Landolt C 320 when the DAC of the test image 300 is 175, the eyesight age of the user may be determined to be 33, as illustrated in FIG. 3C.

Once the eyesight age of a user is determined in the aforementioned manner, the control module 120 provides the user with the result of the determination using the output module 130.

If more than one test image is stored in the storage module 140, operations S220 through S240 of FIG. 2 may be performed repeatedly on one or more test images chosen by the user or a predefined number of test images.

If the user wishes to determine his/her eyesight age using n number of test images, operations S220 through S240 can be performed on each of the n number of test images, thereby obtaining n number of eyesight ages in operation S250. In this case, the control module 120 may determine an average of the n number of eyesight ages as a final eyesight age. However, it is understood that aspects of the present invention are not limited to this method of determining the final eyesight age. For example, the control module 120 may also determine a weighted sum of the n number of eyesight ages as the final eyesight age.

The test image 300 illustrated in FIG. 3A includes a blue Landolt C and a gray background, but aspects of the present invention are not limited thereto. That is, any image including an object (such as a character, a symbol, or a geometrical figure) and a background can be used as a test image as long as the colors (hues, brightnesses, or chromas) of the background and the object can both be varied. Referring to FIG. 3A, the color of an object (i.e., the Landolt C 320) is varied while the color of the background screen 310 is fixed. Alternatively, the color of an object in a test image may be fixed, and the color of a background of the test image may be varied. Still alternatively, the color of an object in a test image and the color of a background of the test image may both be varied.

A variety of test images other than the test image 300 illustrated in FIG. 3A can be stored in the storage module 140. Examples of the test images that can be stored in the storage module 140 are illustrated in FIGS. 4A, 4B, 5, 6A, and 6B.

FIGS. 4A-4B present test images having a contrast pattern according to an embodiment of the present invention. Referring to FIG. 4A, a user may obtain a test image having a preferred contrast pattern by moving a pointer 412 in a slide bar 410 laterally. Specifically, a test image 420 is obtained as originally provided by placing the pointer 412 on the far left of the slide bar 410. Furthermore, a varied test image 430 is obtained by placing the pointer 412 at the center of the slide bar 410, and another varied test image 440 is obtained by placing the pointer 412 on the far right of the slide bar 410. FIG. 4B presents a test image with a varying contrast pattern according to another embodiment of the present invention.

FIG. 5 presents a test image for adjusting chroma. Referring to FIG. 5, a user can vary the chroma of a test patch 530 by moving a pointer in a slide bar 510 laterally so that the test patch 530 has the same chroma as a reference patch 520.

FIGS. 6A and 6B present test images for determining user preferences. Specifically, FIG. 6A presents test images for determining a yellow preference, and FIG. 6B presents test images for determining a sharpness preference.

Referring to FIG. 6A, a user can vary the hue of a test image using a slide bar, thereby obtaining a test image having a preferred hue. Referring to FIG. 6B, a user can vary the sharpness of a test image using a slide bar, thereby obtaining a test image having a preferred sharpness.

Each of the test images illustrated in FIGS. 4A through 6B may have age-specific response information. The age-specific response information of each of the test images illustrated in FIGS. 4A through 6B may be stored in the storage module 140 in advance. Accordingly, the age-specific response information of each of the test images can be used along with user adjustment information input via the user input module 110 to determine the eyesight age of a user.

Figure 7:
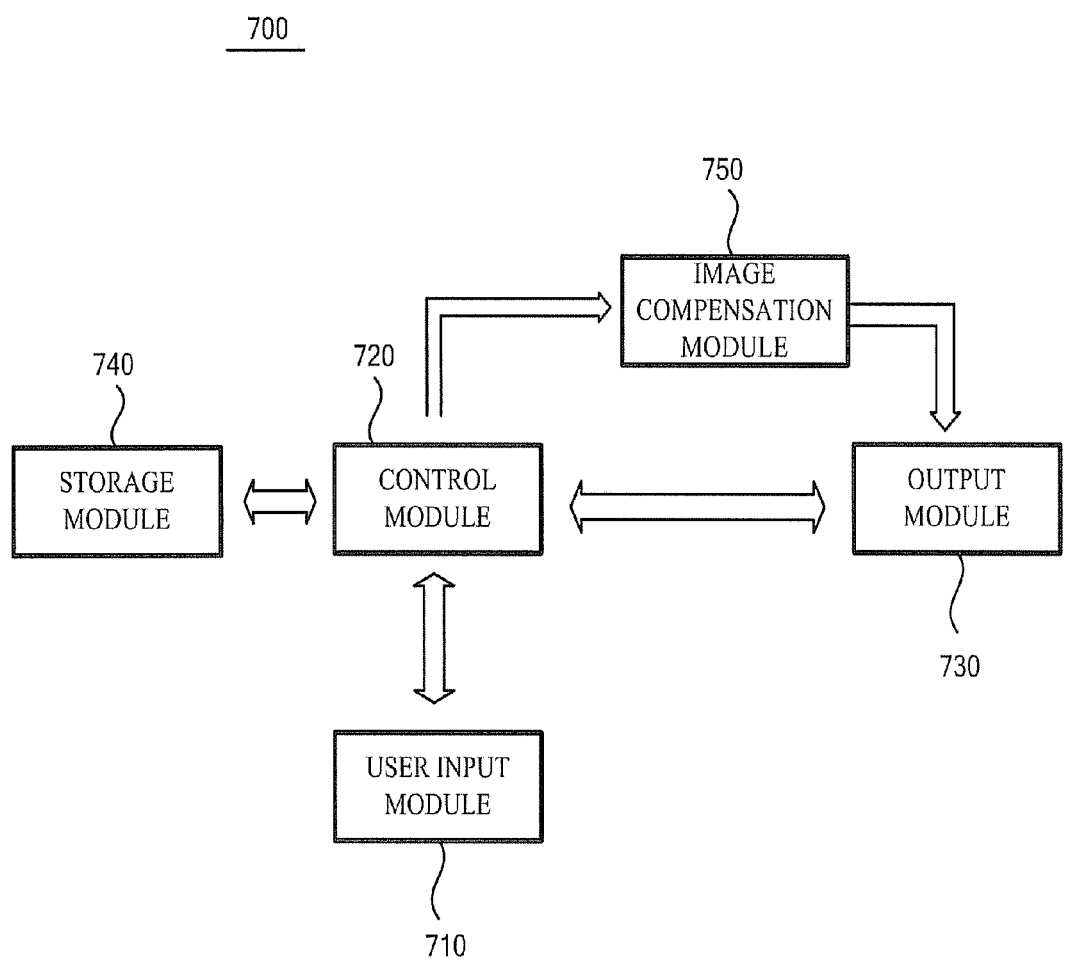
FIG. 7 is a block diagram of an apparatus for determining an eyesight age according to another embodiment of the present invention.

FIG. 7 is a block diagram of an apparatus 700 for determining an eyesight age according to another embodiment of the present invention. Referring to FIG. 7, the apparatus 700 includes a user input module 710, a control module 720, an output module 730, a storage module 740, and an image compensation module 750. The user input module 710, the control module 720, the output module 730, and the storage module 740 respectively correspond to the user input module 110, the control module 120, the output module 130, and the storage module 140 illustrated in FIG. 1. The image compensation module 750 determines an image enhancement parameter based on an eyesight age determined by the control module 120 and image information regarding an original input image. Then, the image compensation module 750 compensates for the eyesight age by modifying the original input image according to the image enhancement parameter. Thus, it is possible to provide a user with an optimum image for the eyesight age of the user on the output module 730.

Specifically, when an original input image is received, the image compensation module 750 determines an image enhancement parameter for providing an optimum image for an eyesight age determined by the control module 720. The image enhancement parameter is a parameter for enhancing the hue, chroma, and/or contrast of an image. That is, the image enhancement parameter determines an amount of image enhancement, such as a hue shift, chroma increase, and/or contrast enhancement. According to the present embodiment, the original input image is modified according to the image enhancement parameter, thereby providing a user with an optimum image.

For example, a hue shift process increases or decreases the hue of an original input image in a direction of a hue preferred by a user in a color coordinate system according to the eyesight age of the user. Accordingly, the preferred hue becomes more apparent in the original input image. The amount by which the hue of an original input image is increased corresponds to the image enhancement parameter. In order to determine the eyesight age of a user, test images (such as those illustrated in FIG. 6A) can be used.

Furthermore, a chroma increase process increases or decreases the chroma of an original input image according to the eyesight age of a user. In order to determine the eyesight age of a user, test images (such as those illustrated in FIG. 5) can be used.

A contrast enhancement process enhances the contrast of an original input image according to the eyesight age of a user. The contrast enhancement process may be performed according to a second line 810 illustrated in FIG. 8 and described below.

Figure 8:
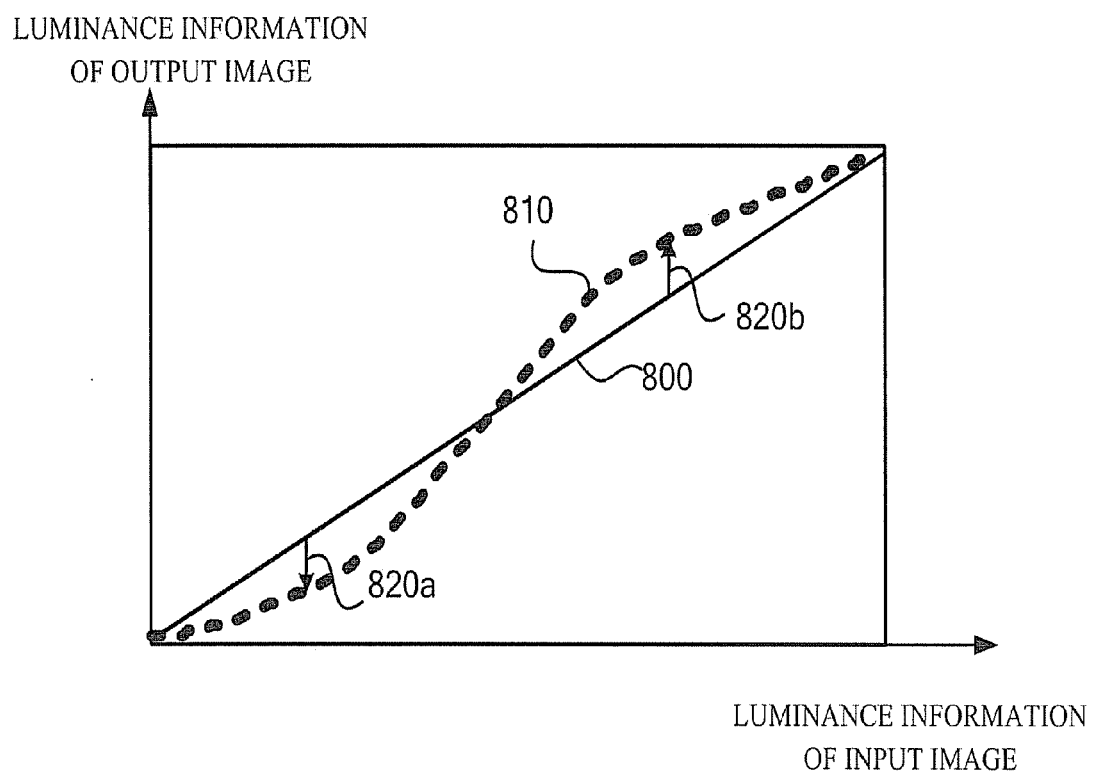
FIG. 8 is a graph for explaining the modification of an image through contrast enhancement according to an embodiment of the present invention.

Referring to FIG. 8, a first line 800 corresponds to an input image that is output without modification. Thus, luminance information of the input image is the same as luminance information of an output image. Referring to the second line 810, the pixel value of a high-luminance portion of the input image is increased, and the pixel value of a low-luminance portion of the input image is reduced. According to the present embodiment, a contrast enhancement operation may be performed using the second line 810. Referring to FIG. 8, compensation amounts 820a and 820b may vary according to the eyesight age determined by the control module 720.

The determination of an eyesight age according to another embodiment of the present invention will hereinafter be described in detail with reference to FIGS. 9 through 14. FIG. 9 is a diagram explaining the basic concept of the determination of an eyesight age according to another embodiment of the present invention. Referring to FIG. 9, a user may move a pointer in a bar controller 920 laterally and fix the pointer when a preferred modification of the image is displayed on a display screen 910. As a result of such simple manipulation, the eyesight age of the user can be determined.

In detail, as the user moves the pointer laterally in the bar controller 920, the properties of an image displayed on the display screen 910 (such as luminance, chroma, contrast, and hue) vary gradually. It is understood that, according to aspects of the present invention, the moving of the pointer may change just one property or may change a plurality of properties. Furthermore, it is understood that multiple bar controllers may be provided, each corresponding to one or more properties. The user may stop moving the pointer when a preferred modification of the image is displayed on the display screen 910. The preferred modification of the image may be interpreted as an image whose visibility is optimized for the user.

Once the user chooses a preferred modification of the image by fixing the location of the pointer in the bar controller 920, an eyesight age corresponding to the chosen preferred modification of the image is provided to the user. Therefore, the user can easily determine his/her eyesight age through the manipulation of the bar controller 920.

Figure 10:
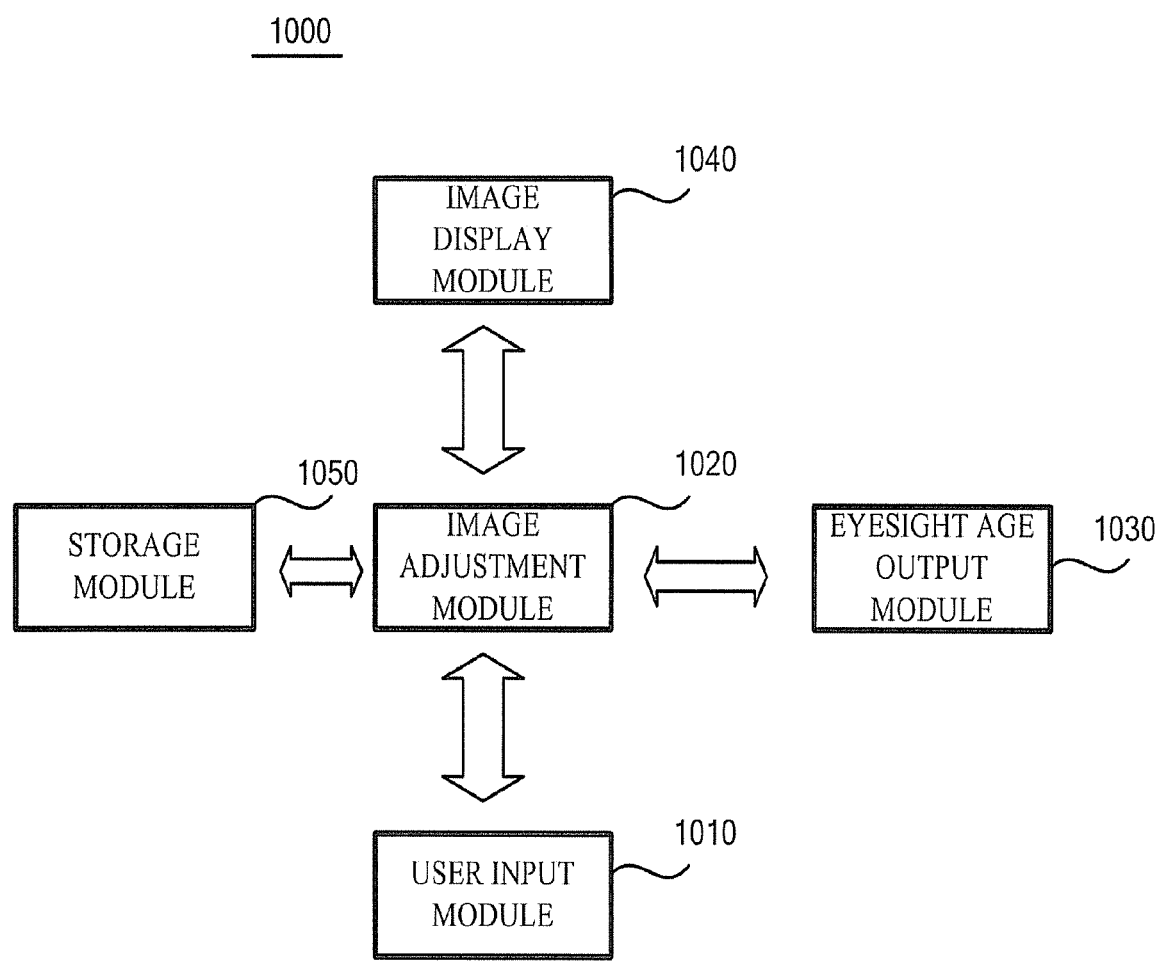
FIG. 10 is a block diagram of an apparatus for determining an eyesight age according to another embodiment of the present invention.

FIG. 10 is a block diagram of an apparatus 1000 for determining an eyesight age according to another embodiment of the present invention. Referring to FIG. 10, the apparatus 1000 includes a user input module 1010, an image adjustment module 1020, an eyesight age output module 1030, an image display module 1040, and a storage module 1050.

The user input module 1010 receives user input information for modifying an image and provides the user input information.

The image adjustment module 1020 receives the user input information provided by the user input module 1010, and modifies the image according to the user input information. Also, the image adjustment module 1020 provides an eyesight age corresponding to the modified image.

The eyesight age output module 1030 outputs the eyesight age corresponding to the modified image.

The image display module 1040 displays the modified image to the user.

The storage module 1050 stores an eyesight age and an image parameter corresponding to each user input information.

The operations of the user input module 1010, the image adjustment module 1020, the eyesight age output module 1030, the image display module 1040, and the storage module 1050 will hereinafter be described in further detail with reference to FIG. 11.

Figure 11:
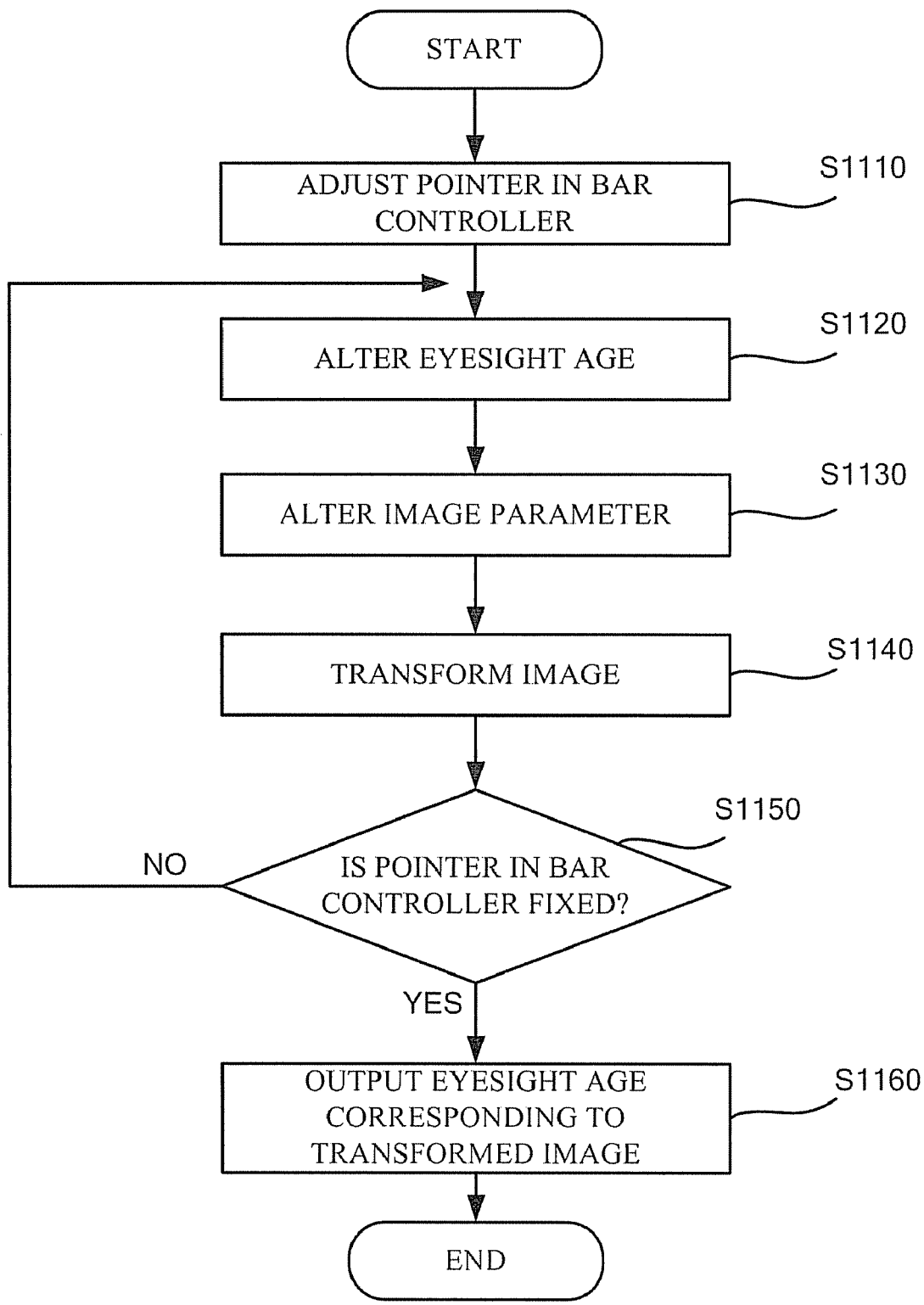
FIG. 11 is a flowchart illustrating a method of determining an eyesight age according to another embodiment of the present invention.

Referring to FIG. 11, in operation S1110, a user manipulates the user input module 1010 in order to modify an image displayed by the image display module 1040. For example, in operation S1110, the user may provide user input information through a manipulation of a bar controller 920, as illustrated in FIG. 9. That is, the user input information may correspond to the location of a pointer in the bar controller 920.

In operation S1120, the image adjustment module 1020 alters an eyesight age according to the user input information. Specifically, the image adjustment module 1020 extracts an eyesight age corresponding to the user input information from the storage module 1050 and changes a previous eyesight age corresponding to previous user input information to the extracted eyesight age.

In operation S1130, the image adjustment module 1020 extracts, from the storage module 1050, an image parameter value corresponding to the eyesight age altered by the image adjustment module 1020, and changes an image parameter value corresponding to the previous eyesight age to the extracted image parameter value. In operation S1140, the image adjustment module 1020 modifies an image currently being displayed by the image display module 1040 by applying the extracted image parameter value.

According to the present embodiment, an image parameter that is needed to modify an image may be determined through experimentation on a plurality of people having different ages, and then stored in the storage module 1050 in advance.

Figure 12:
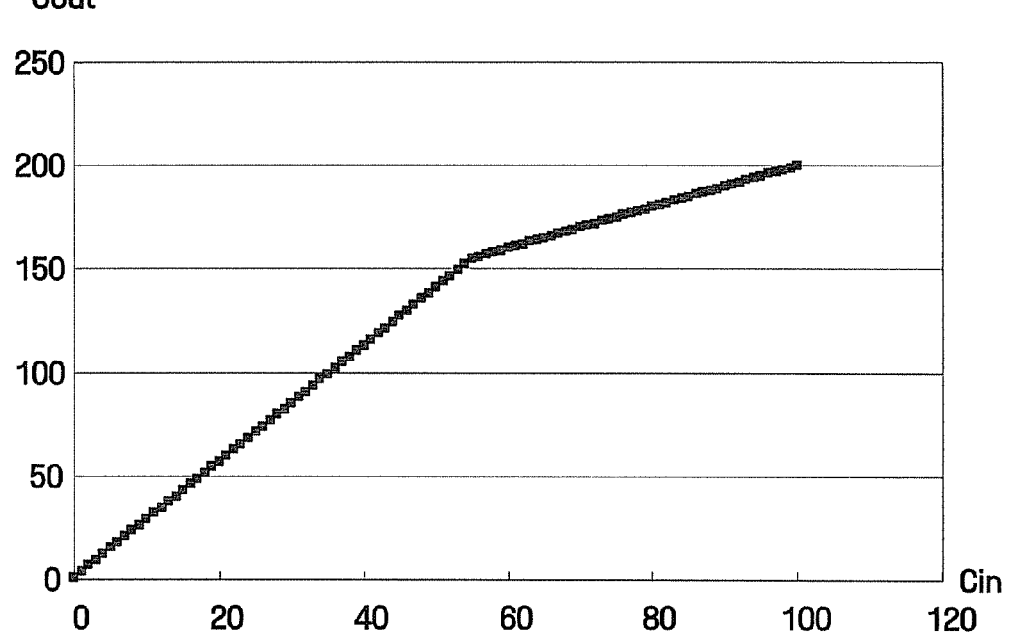
FIG. 12 is a diagram explaining an image parameter that represents a chroma property, according to an embodiment of the present invention.

The image parameter may be an image parameter that represents a chroma, contrast, luminance, and/or hue property. An example of an image parameter that represents a chroma property will hereinafter be described in detail with reference to FIG. 12. Referring to FIG. 12, the horizontal axis scales the chroma of an arbitrary pixel between 0 and 100, and the vertical axis represents a relative chroma enhancement value for each pixel. A graph illustrated in FIG. 12 can be used as an image parameter corresponding to an arbitrary eyesight age.

The storage module 1050 may store such a graph as the one illustrated in FIG. 12 for each eyesight age as an image parameter that represents a chroma property. For example, the image adjustment module 1020 transforms the image currently being displayed by the image display module 1040 according to a graph corresponding to the altered eyesight age provided by the image adjustment module 1020.

An example of an image parameter that enhances both brightness and contrast properties at the same time will hereinafter be described in detail with reference to FIG. 13. For example, referring to FIG. 13, the length of a first section 1302 and a difference between an output pixel value Q3 and an output pixel value Q2 that correspond to an input pixel value P2 belonging to a second section 1304 (i.e., |Q3−Q2|) may be adjusted according to the pattern of distribution of pixel values of an input image. For example, if most pixel values of the input image are distributed in a low-luminance area, the length of the first section 1302 and |Q3−Q2| may both be reduced.

Figure 13:
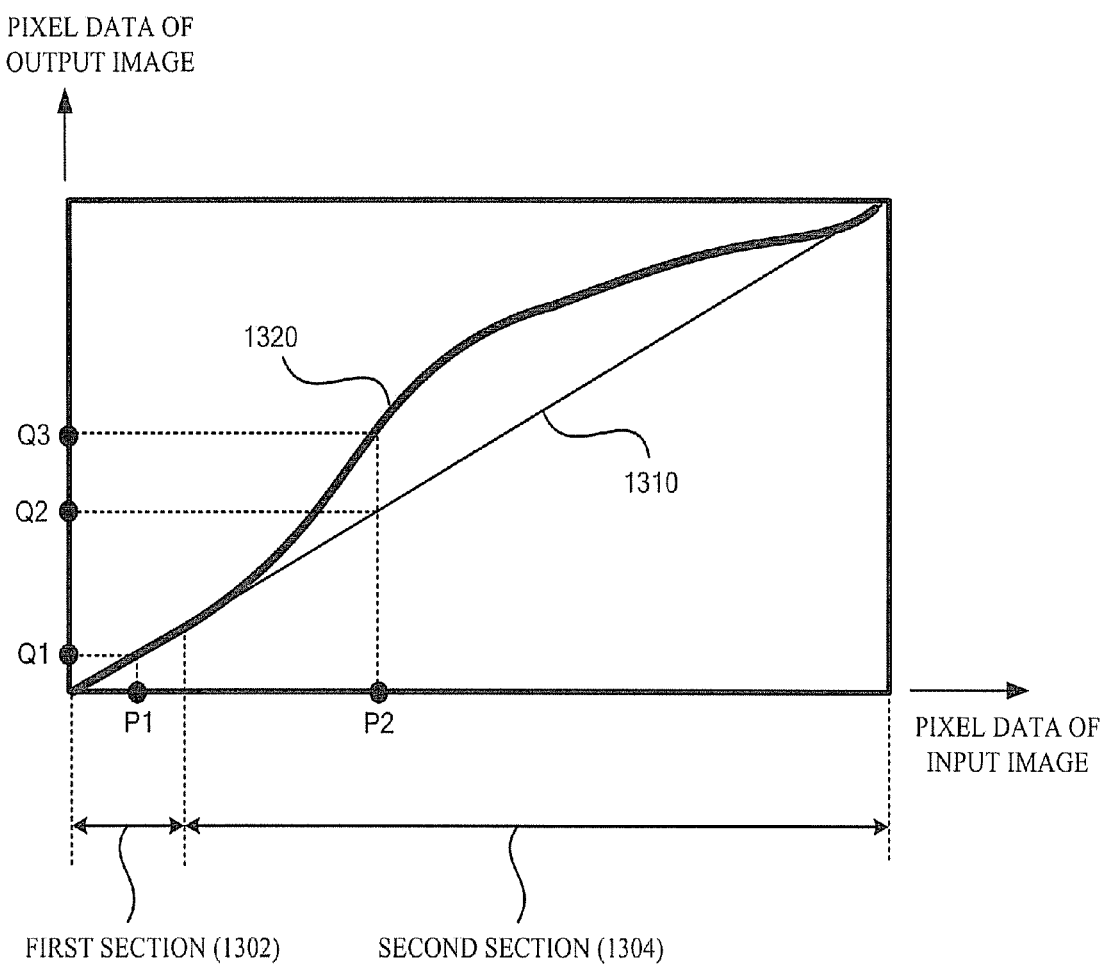
FIG. 13 is a diagram explaining an image parameter that enhances both lightness and contrast properties at the same time, according to an embodiment of the present invention.

Referring to FIG. 13, a first line 1310 corresponds to an input image that is not modified, and a second line 1320 corresponds to an input image that is modified. For example, assuming that each pixel of the input image is represented by eight bits, the input image may have a total of 256 ($=2^8$) pixel data.

The pixel data of the input image may be classified as belonging to one of two sections (i.e., one of the first section 1302 and the second section 1304). Pixel values belonging to the first section 1302 are converted according to the first line 1310. In this case, the input image is not substantially modified. Pixel values belonging to the second section 1304 are increased by a predetermined amount.

In detail, since the input pixel value P1 belongs to the first section 1302, the input pixel value P1 is converted into the output pixel value Q1 according to the first line 1310 without the need to be modified. On the other hand, since the input pixel value P2 belongs to the second section 1304, the input pixel value P2 is converted into the output pixel value Q3, rather than into the output pixel value Q2, according to the second line 1320. That is, the input pixel value P2 is increased by |Q2−Q3|.

FIG. 13 illustrates the variation of each pixel data of an input image. The variation of pixel data of the input image may be interpreted as the variation of the luminance of each pixel of the input image. That is, pixels of an input image with lower luminance values than a predefined threshold are not subject to image compensation, whereas pixels of the input image with higher luminance values than the predefined threshold are increased by a predetermined compensation amount.

Therefore, the storage module 1050 may store such a graph as the graph illustrated in FIG. 13 for each eyesight age as an image parameter that represents both brightness and contrast properties. The image adjustment module 1020 modifies the image currently being displayed by the image display module 1040 according to a graph corresponding to the altered eyesight age provided by the image adjustment module 1020. An image parameter that represents other properties (such as a hue property) may also be stored in the storage module 1020 as a graph for each eyesight age.

Referring to FIG. 11, in operation S1150, the image adjustment module 1020 determines whether the user input information provided by the user input module 1010 is uniformly maintained for a predetermined amount of time (i.e., whether the location of the pointer in the bar controller is currently fixed). In operation S1160, if the location of the pointer in the bar controller is currently fixed (operation S1150), the image adjustment module 1020 outputs an eyesight age corresponding to the transformed image provided by the image adjustment module 1020 via the eyesight age output module 1030. The fixing of the location of the pointer in the bar controller may occur when the user selects a most preferred modification of the image. The eyesight age of the user is determined based on the most preferred modification of the image selected by the user. It is understood that the most preferred modification may be determined by methods other than based on whether the location of the pointer in the bar controller is fixed for a predetermined amount of time. For example, a user may press a button indicating a selection of a most preferred modification of the image.

The eyesight age output module 1030 may output an eyesight age that is determined based on an image preferred by the user using a visual or auditory method. For example, the eyesight age output module 1030 may output an eyesight age via a screen of the apparatus 1000 or via a speaker of the apparatus 1000 as a sound.

If the pointer is still being moved in the bar controller (operation S1150), rather than being fixed to a certain location in the bar controller, operations S1120 through S1150 are performed again until the user selects a preferred modification of the image. That is, the modification of the image currently being displayed by the image display module 1040 continues until the user selects a preferred modification of the image.

According to aspects of the present embodiment, a bar controller is used as the user input module 1010. However, aspects of the present invention are not limited thereto. That is, any type of input tool (e.g., four direction keys or number keys on a mobile phone) that can transform an image displayed by the image display module 1040 can be used as the user input module 1010.

According to aspects of the present invention, it is possible to provide a user with an entertainment function by determining the eyesight age of the user through simple manipulation of an input module and displaying the result of the determination to the user. In addition, according to aspects of the present invention, it is possible to enhance an original input image by adjusting properties of the original input image (such as the hue, chroma, and/or contrast) according to the eyesight age of a user.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An apparatus to determine an eyesight age, the apparatus comprising:
   a storage module to store at least one test image and age-specific response information for the at least one test image;
   a control module to receive user adjustment information indicating a variation in the at least one test image, and to determine an eyesight age of a user based on the user adjustment information and the age-specific response information; and
   an output module to output the determined eyesight age,
   wherein the age-specific response information comprises information indicating a relationship between a correct answer probability regarding the at least one test image and a pixel value of the at least one test image.

2. The apparatus as claimed in claim 1, wherein the variation in the at least one test image corresponds to a variation in the pixel value of the at least one test image.

3. The apparatus as claimed in claim 2, wherein a first pixel value at a specific correct answer probability corresponds to a first eyesight age, and a second pixel value at the specific correct answer probability corresponds to a second eyesight age.

4. The apparatus as claimed in claim 1, wherein the age-specific response information indicates a first eyesight age corresponding to a first user adjustment information and a second eyesight age corresponding to a second user adjustment information.

5. The apparatus as claimed in claim 1, wherein a first test image comprises a background screen and an object having a predetermined shape.

6. The apparatus as claimed in claim 5, wherein the object is a blue Landolt C, the object initially has first color, which is a same color as the background screen, and the user adjustment information corresponds to a modification to the first color of the object by a user such that the Landolt C is properly recognized against the background screen by the user.

7. The apparatus as claimed in claim 1, wherein a first test image is an image comprising a contrast pattern.

8. The apparatus as claimed in claim 1, wherein a first test image comprises a test patch and a reference patch such that the user adjusts the test patch to have a same chroma as the reference patch.

9. The apparatus as claimed in claim 1, wherein the user modifies the at least one test image to determine an image preferred by the user.

10. The apparatus as claimed in claim 1, wherein, if the eyesight of the user is determined based on n number of test images, where n is a natural number greater than 1, the control module determines n number of eyesight ages based on the respective n number of test images, and determines the eyesight age of the user output by the output module based on the n number of eyesight ages.

11. The apparatus as claimed in claim 10, wherein the control module determines an average of the n number of eyesight ages as the eyesight age of the user output by the output module.

12. The apparatus as claimed in claim 1, further comprising:
   an image compensation module to determine an image enhancement parameter based on the determined eyesight age and image information of an original input image, and to modify the original input image according to the image enhancement parameter,
   wherein the output module outputs the modified image provided by the image compensation module.

13. The apparatus as claimed in claim 12, wherein the image enhancement parameter comprises an image parameter that modifies at least one of a hue property, a chroma property, and a contrast property of the original input image.

14. A method of determining an eyesight age, the method comprising:
   receiving user adjustment information from a user indicating a variation in at least one test image; and
   determining the eyesight age of the user based on the user adjustment information,
   wherein the determining of the eyesight age comprises determining the eyesight age of the user based on the user adjustment information and age-specific response information; and
   the age-specific response information comprises information indicating a relationship between a correct answer probability regarding the at least one test image and a pixel value of the at least one test image.

15. The method as claimed in claim 14, further comprising: outputting the determined eyesight age.

16. The method as claimed in claim 14, wherein: the variation in the at least one test image corresponds to a variation in the pixel value of the at least one test image.

17. The method as claimed in claim 14, wherein a first pixel value at a specific correct answer probability corresponds to a first eyesight age, and a second pixel value at the specific correct answer probability corresponds to a second eyesight age.

18. The method as claimed in claim 14, wherein the age-specific response information indicates a first eyesight age corresponding to a first user adjustment information and a second eyesight age corresponding to a second user adjustment information.

19. The method as claimed in claim 14, wherein a first test image comprises a background screen and an object having a predetermined shape.

20. The method as claimed in claim 19, wherein the object is a blue Landolt C, the object initially has first color, which is a same color as the background screen, and the user adjustment information corresponds to a modification to the first color of the object by a user such that the Landolt C is properly recognized against the background screen by the user.

21. The method as claimed in claim 14, wherein a first test image is an image comprising a contrast pattern.

22. The method as claimed in claim 14, wherein a first test image comprises a test patch and a reference patch such that the user adjusts the test patch to have a same chroma as the reference patch.

23. The method as claimed in claim 14, wherein the user modifies the at least one test image to determine an image preferred by the user.

24. The method as claimed in claim 14, further comprising:
determining an image enhancement parameter based on the determined eyesight age and image information of an original input image; and
modifying the original input image according to the image enhancement parameter.

25. The method as claimed in claim 24, wherein the image enhancement parameter comprises an image parameter that modifies at least one of a hue property, a chroma property, and a contrast property of the original input image.

26. A computer readable recording medium encoded with the method of claim 14 implemented by a computer.

27. A method of determining an eyesight age, the method comprising:
receiving user adjustment information from a user indicating a variation in at least one test image; and
determining the eyesight age of the user based on the user adjustment information,
wherein:
the receiving of the user adjustment information comprises receiving user adjustment information from the user indicating variations in n number of test images, where n is a natural number greater than 1; and
the determining of the eyesight age comprises:
determining n number of eyesight ages based on the respective n number of test images; and
determining a final eyesight age of the user based on the n number of eyesight ages.

28. The method as claimed in claim 27, wherein the determining of the final eyesight age comprises determining an average of the n number of eyesight ages as the final eyesight age.

29. A method of determining an eyesight age, the method comprising:
receiving user adjustment information from a user indicating a variation in at least one test image;
determining the eyesight age of the user based on the user adjustment information and age-specific response information;
determining an image enhancement parameter based on the determined eyesight age and image information of an original input image;
modifying the original input image according to the image enhancement parameter;
and outputting the compensated image,
wherein the age-specific response information comprises information indicating a relationship between a correct answer probability regarding the at least one test image and a pixel value of the at least one test image.

30. The method as claimed in claim 29, wherein the variation in the at least one test image corresponds to a variation in the pixel value of the at least one test image.

31. The method as claimed in claim 30, wherein a first pixel value at a specific correct answer probability corresponds to a first eyesight age, and a second pixel value at the specific correct answer probability corresponds to a second eyesight age.

32. The method as claimed in claim 29, wherein the image enhancement parameter comprises an image parameter that enhances at least one of: a hue property, a chrome property, and a contrast property of the original input image.

33. A computer readable recording medium encoded with the method of claim 29 implemented by a computer.

34. An apparatus for determining an eyesight age, the apparatus comprising:
a user input module to receive user input information from a user;
an image adjustment module to modify an image according to the user input information, and to determine an eyesight age of the user corresponding to the user input information of a preferred modification of the image set by the user; and
an image display module to display the modified image,
wherein the image adjustment module modifies the image, displayed by the image display module, according to an image parameter that is determined according to the user input information, and
wherein the image parameter is determined according to the eyesight age corresponding to the user input information.

35. The apparatus as claimed in claim 34, further comprising:
an eyesight output module to output the eyesight age.

36. The apparatus as claimed in claim 34, wherein the image adjustment module determines the modified image to be the preferred modification of the image if the user input information is uniformly maintained for a predetermined amount of time.

37. The apparatus as claimed in claim 34, wherein the image parameter comprises a parameter that represents at least one of a contrast property, a luminance property, a hue property, and a chroma property.

38. The apparatus as claimed in claim 34, wherein the user input module comprises a bar controller.

39. A method of determining an eyesight age, the method comprising:
receiving user input information from a user;
modifying an image according to the user input information and displaying the modified image; and determining an eyesight age of the user corresponding to the user input information of a preferred modification of the image set by the user, wherein the modifying of the image comprises modifying the image according to an image parameter that is determined according to the user input information, and wherein the image parameter is determined according to the eyesight age corresponding to the user input information.

40. The method as claimed in claim 39, further comprising: outputting the eyesight age.

41. The method as claimed in claim 39, wherein the determining of the eyesight age of the user comprises determining the modified image to be the preferred modification of the image if the user input information is uniformly maintained for a predetermined amount of time.

42. The method as claimed in claim 39, wherein the image parameter comprises a parameter that represents at least one of a contrast property, a luminance property, a hue property, or a chroma property.

43. The method as claimed in claim 39, wherein the receiving of the user input information comprises receiving the user input information via a bar controller.

44. A computer readable recording medium encoded with the method of claim 39 implemented by a computer.

45. An apparatus for determining an eyesight age, the apparatus comprising:

a storage module to store at least one test image and age-specific response information for the at least one test image;

a control module to receive user adjustment information indicating a variation in the at least one test image, and to determine an eyesight age of a user based on the user adjustment information and the age-specific response information;

an image compensation module to determine an image enhancement parameter based on the determined eyesight age and image information of an original input image, and to modify the original input image according to the image enhancement parameter; and an output module to output the modified image provided by the image compensation module, wherein the age-specific response information comprises information indicating a relationship between a correct answer probability regarding the at least one test image and a pixel value of the at least one test image.

46. The apparatus as claimed in claim 45, the variation in the at least one test image corresponds to a variation in the pixel value of the at least one test image.

47. The apparatus as claimed in claim 45, wherein the image enhancement parameter comprises an image parameter that modifies at least one of a hue property, a chroma property, and a contrast property of the original input image.

* * * * *

UNITED STATES PATENT AND TRADEMARK OFFICE
CERTIFICATE OF CORRECTION

PATENT NO.        : 7,654,673 B2                                    Page 1 of 1
APPLICATION NO. : 11/830234
DATED             : February 2, 2010
INVENTOR(S)       : Gee-young Sung et al.

It is certified that error appears in the above-identified patent and that said Letters Patent is hereby corrected as shown below:

Column 1, Line 8, change "2006-73383" to --10-2006-73383--.

Column 1, Line 8, change "-2006-109509" to --10-2006-109509--.

Column 14, Lines 12-13, change
"enhancement parameter;
and outputting the compensated image," to
--enhancement parameter; and
outputting the compensated image,--.

Column 14, Line 28, change "chrome" to --chroma--.

Column 16, Line 20, after "claim 45," insert --wherein--.

Signed and Sealed this

Eleventh Day of May, 2010

David J. Kappos
*Director of the United States Patent and Trademark Office*